United States Patent [19]
Sawyer

[11] 4,065,816
[45] Jan. 3, 1978

[54] SURGICAL METHOD OF USING A STERILE PACKAGED PROSTHESIS

[76] Inventor: Philip Nicholas Sawyer, 7600 Ridge Blvd., Brooklyn, N.Y. 11209

[21] Appl. No.: 741,476

[22] Filed: Nov. 12, 1976

Related U.S. Application Data

[62] Division of Ser. No. 579,791, May 22, 1975, Pat. No. 4,011,947.

[51] Int. Cl.$^2$ ............................................. A61F 1/22
[52] U.S. Cl. .................................. 3/1.5; 128/303 R; 53/21 FC; 53/21 R; 3/1
[58] Field of Search ............... 3/1, 1.5; 128/303 R, 128/334 R; 206/363, 438; 220/4 B, 4 E; 53/21 FC, 21 R

[56] References Cited
U.S. PATENT DOCUMENTS

| | | | |
|---|---|---|---|
| 1,724,516 | 8/1929 | Remedios | 206/362.2 X |
| 3,409,013 | 11/1968 | Berry | 3/1.5 X |
| 3,476,506 | 11/1969 | Andersen et al. | 53/21 FC |
| 3,587,115 | 6/1971 | Shiley | 3/1.5 |
| 3,828,787 | 8/1974 | Anderson et al. | 3/1.5 X |
| 3,861,395 | 1/1975 | Taniquchi | 206/438 X |

OTHER PUBLICATIONS

"The Influence of the Metal Interface Charge on Long-Term Function of Prosthetic Heart Valves" by P. N. Sawyer et al., Prosthetic Heart Valves, Charles C. Thomas-Publisher, Springfield, Ill., 1968, pp. 198-220.

*Primary Examiner*—Ronald L. Frinks
*Attorney, Agent, or Firm*—Alan K. Roberts

[57] ABSTRACT

A method is provided for packaging a prosthetic device for surgical use. The method includes detachably coupling a support to the device, cleaning substantially all of the foreign material from the device, and encapsulating the thusly cleaned device in an openable capsule with the support extending therethrough. The encapsulated device and support attached thereto are further encased in a bag or other like protective device and this packaged assembly is further encased in a box. Sterilization of the whole is effected by means of radiation. As to cleaning of the prosthetic device, this is effected by electropolishing, chemical polishing, electrochemical polishing or cathodic cleaning or the like. For use, the bagged device is subsequently removed from the box and delivered to an operating room or other antiseptic environment whereat the bag is removed and the device handled by means of the support attached thereto. A solution containing, for example, heparin and an antibiotic is injected into the capsule for treating the prosthetic device. Afterwards, the capsule is opened and the prosthetic device is juxtaposed to an installation zone by means of the support.

5 Claims, 8 Drawing Figures

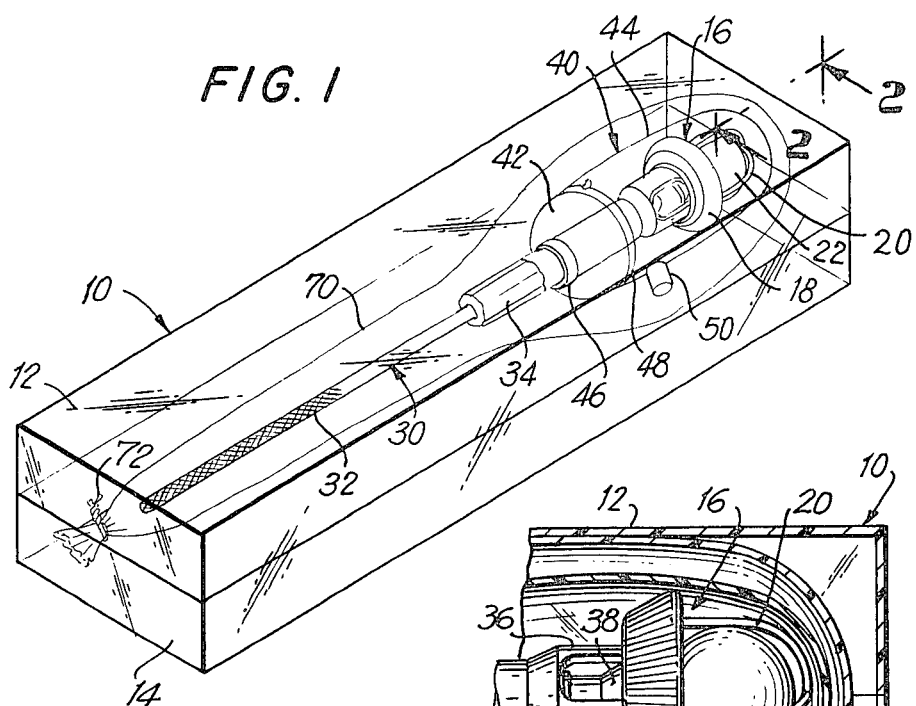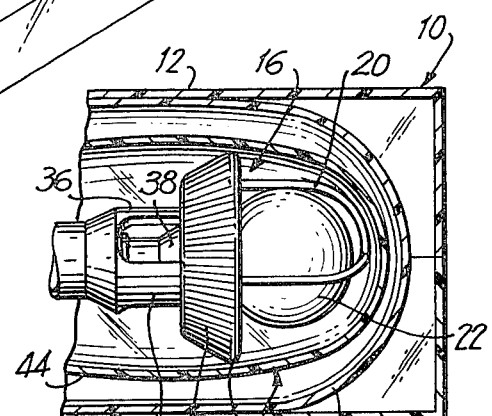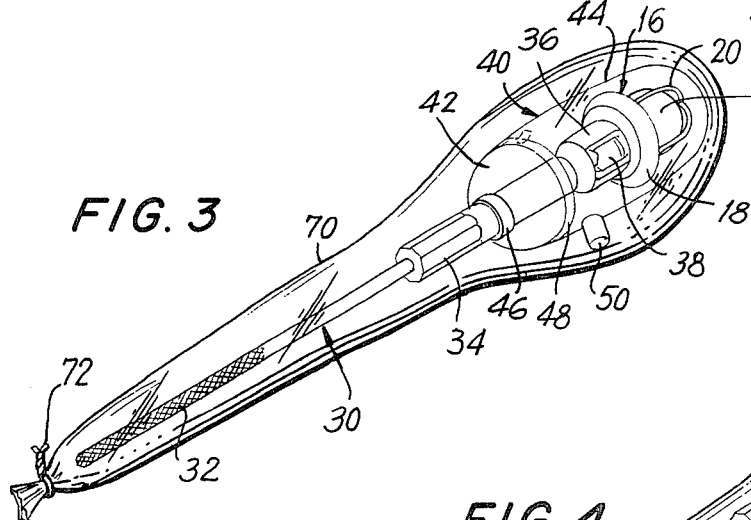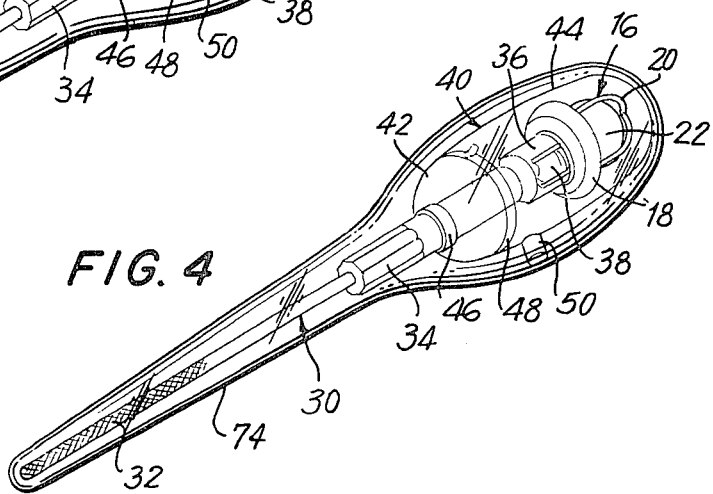

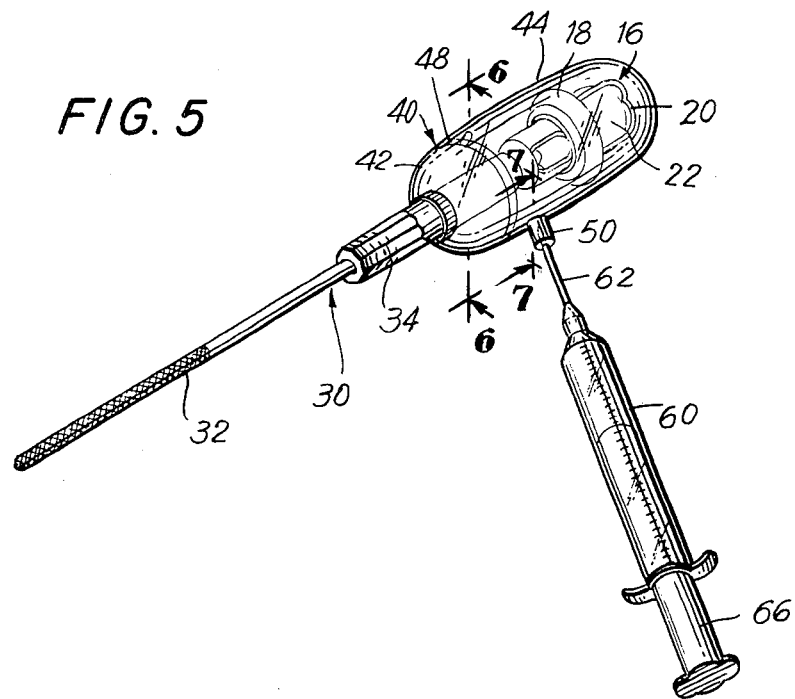
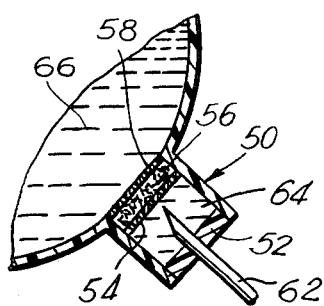
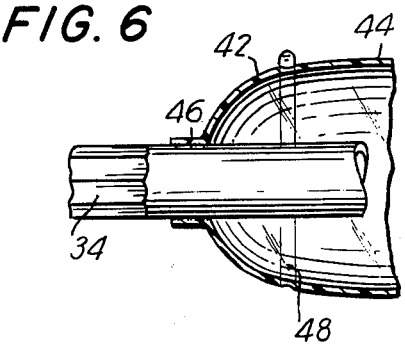
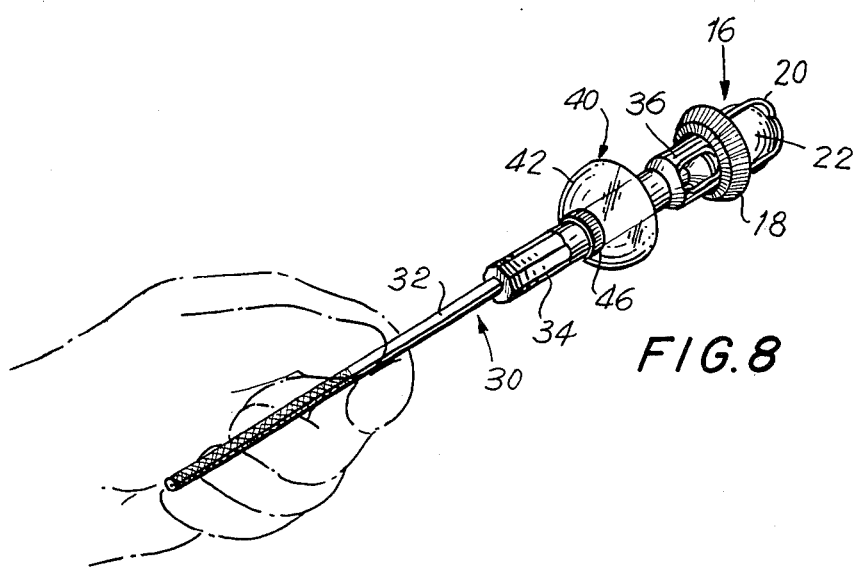

SURGICAL METHOD OF USING A STERILE PACKAGED PROSTHESIS

CROSS RELATED APPLICATION

This Application is a division of application Ser. No. 579,791 filed May 22, 1975, now U.S. Pat. No. 4,011,947.

FIELD OF INVENTION

This invention relates to methods of packaging prosthetic devices and to the packaged prosthetic devices resulting therefrom and to methods of using the same. The invention is particularly suitable for use with prosthetic devices such as, for example, heart replacement valves.

BACKGROUND

Prosthetic devices such as heart replacement valves are generally manufactured in a non-sterile atmosphere. They are then placed in plastic bags and shipped in openable plastic boxes to the ultimate user who may be a surgeon in a hospital. The boxes may be suitably provided with sponge rubber mats or the like to prevent damage to the prosthetic devices by reason of jarring action thereagainst.

In the hospital, the prosthetic device is removed manually from the box and from the bag in which it has been packed and is ultimately autoclaved. This autoclaving operation may sometimes take place in a container or it may, for example, take place in a rack. The autoclaving is usually effected in an area adjacent the operating room in which is performed the surgical procedure which results in the installation of the prosthetic device. The autoclaving operation takes care of sterilizing the prosthetic device but does not take care of degreasing the device nor of removing foreign substances as will further be discussed hereinbelow.

The prosthetic device when taken out of the autoclave is usually handled with sterile tongs or the like and is handed to a scrub nurse who may pick it up with a sterilized, gloved hand and who may then, in the case of a heart replacement valve, for example, drop it into a beaker containing a physiologic saline solution or a Ringers solution containing antibiotics and the like.

As a result of the above type of procedure, the prosthetic device is progressively sterilized but becomes increasingly covered by grease and other foreign material which is harmful to the acceptance of the prosthetic device in the environment into which it is to be placed. In this relatively dirty form, the heart replacement valve or other such prosthetic device is handed to the surgeon for implantation.

The "dirt" does not cause infection but leads to a number of other disadvantageous results. For example, this dirt may cause thrombosis or it may cause abnormal fibroplasia or it may possibly increase a subsequent tendency towards infection.

SUMMARY OF INVENTION

It is an object of the invention to provide an improved method of packaging prosthetic devices to avoid the above-noted difficulties.

It is another object of the invention to provide an improve packaged prosthetic device.

Still another object of the invention is to provide an improved method of employing the packaged prosthetic device of the invention.

Still another object of the invention is to provide an improved packaging technique which provides that a prosthetic device will arrive at its ultimate position for installation in a sterile and clean condition most suited for optimum performance.

In achieving the above and other objects of the invention, there is provided a method of packaging a prosthetic device for surgical use which method comprises detachably coupling a support such as a mandrel to the device, cleaning substantially all foreign material from the device, encapsulating the thusly cleaned device in an openable capsule with the support extending therethrough and sterilizing the support with the thusly encapsulated and cleaned device thereon. The support and cleaned device are preferably encased in a removable protective material before sterilization. The encased support and cleaned device are furthermore preferably placed, prior to sterilization, in an openable box.

According to the invention, the cleaning may be effected by electropolishing, chemical polishing, electrochemical polishing or cathodic cleaning or the like. Sterilization may be effected by radiation with X-rays.

The above-noted capsule may be provided with a substantially uni-directional entrance for a fluid. The capsule may moreover be filled with an inert gas. The capsule may be made in two or more parts, one of which is mounted on the above mentioned support and the other of which is detachably supported on the first said part. These parts are preferably hermetically sealed together.

In accordance with the invention, there is furthermore provided a protected prosthetic device comprising a sterilized and cleaned prosthetic structure, a support detachably engaging said structure and adapted to constitute a handle for the same, and hermetically sealed protective means encapsulating said structure, said support extending hermetically through these means and the means being openable to render the structure accessible. Said means may be supported on the support and will be preferably spaced in entirety from the prosthetic structure. A shielding means may be provided encasing the structure, support and protective means. The shielding means may be, for example, a collapsible plastic bag or it may be a rigid plastic shield. The protective means may be a rigid capsule.

A syringe intravenous needle penetrable port will be provided in the capsule for the injection of a fluid into the capsule. This fluid will be such as to contain, for example, heparin and an antibiotic. Most of the aforesaid means, if not all, will be X-ray radiation penetrable in order to provide for sterilization of the same. An openable box may be provided housing the aforesaid prosthetic structure, capsule and support, all encased in the above-noted shielding means. The prosthetic structure may be, for example, a heart replacement valve.

In further accordance with the invention there is provided a method comprising mounting a prosthetic device on a support and removing at least substantially all foreign substance from the device and support, encapsulating the prosthetic device in a capsule, encasing said device and support in a removable shield, boxing the thusly encased device and support, irradiating the thusly boxed and encased device and support to sterilize the same, sequentially removing the box and shield, injecting a fluid into the capsule to treat the prosthetic device, opening the capsule to expose the device, and maneuvering the device through the support to locate the device proximate a site of installation.

The prosthetic device may, for example, be a heart replacement valve of a type including a ring-structure. In this event the ring will be engaged by a mandrel having the ability to expand in radial direction and to contract to release the ring, the ring being ultimately sutured in position in a cardiac or vascular system whereafter the mandrel is detached from the heart replacement valve, the mandrel being suitable for subsequent use in another procedure.

The above and other objects and advantages of the invention will be apparent from the detailed description which follows hereinafter.

BRIEF DESCRIPTION OF DRAWING

In the drawing:

FIG. 1 is a perspective view of a packaged heart replacement valve provided according to the packaging techniques of the invention;

FIG. 2 is a fragmentary perspective view taken along line 2—2 of FIG. 1;

FIG. 3 is a perspective view of the encased and encapsulated valve of FIG. 1 removed from its box;

FIG. 4 is a perspective view of a variation of the structure illustrated in FIG. 3;

FIG. 5 is a perspective view of the valve of FIG. 1 still supported on its mandrel with provision being made for injection of a solution into the capsule thereof;

FIG. 6 is a fragmentary view in cross-section taken along line 6—6 of FIG. 5;

FIG. 7 is a fragmentary view on enlarged scale and in cross-section taken along line 7—7 of FIG. 5; and FIG. 8 illustrates the valve with a part of the capsule removed with the valve being maneuvered into position adjacent a site for installation.

DETAILED DESCRIPTION

The invention relates generally to prosthetic devices. By way of example, the invention is explained with respect to a heart replacement valve. A number of commercially available valves may be employed in connection with the process of the invention and conversely the invention is applicable for optimizing the use of a number of prosthetic devices.

Among the prosthetic devices with which the use of the invention may be best envisaged are the Starr-Edwards human aortic valve prosthesis, the Bjork-Shiley heart valve replacement, the Smeloff-Cutter heart replacement valve and the like. These valves may be manufactured in a non-sterile atmosphere, placed in plastic bags and shipped to a hospital whereat they are used. They are normally autoclaved and, according to usual hospital procedures, are completely sterilized before they are installed but no provision is made for avoiding the incidence of grease and minor amounts of foreign materials which I have discovered are inimitable to the receipt of such prosthetic devices in the types of environments in which they are to be installed and to exist for extended periods of time.

I have now found that it is possible to package these prosthetic devices in such a manner that they are not contacted manually, either directly by the hand or by the sterilized gloved hand prior to installation with the possible exception of the suturing operation in the case of heart valves whereby a sewing ring structure or valve skirt included in the heart valves is sutured into position.

For the nature of the cleaning and removal of foreign material and grease to which I refer hereinafter, I refer to my co-pending application Ser. No. 399,466, filed Sept. 21, 1973, wherein are particularly disclosed such methods as electro-polishing, chemical polishing, electrochemical polishing and cathodic cleaning which are intended to remove such surface contaminants as oxides, grease and so forth. As set forth in my co-pending application, it is preferred that no foreign particles be present on the surfaces of heart replacement valves or other such prosthetic devices as might be seen by scanning with an electron microscope. More particularly, the surfaces should, as a preferred rule, have no more than two foreign particles not exceeding 0.5 microns in diameter per 25 square microns of surface. If this rule is observed, non-thrombogenic, metal heart valves and the like can be obtained. If this limitation is slightly exceeded, valves and prosthetic devices of improved characteristics may be obtained provided that the number of foreign particles is kept at a minimum.

In FIG. 1 is illustrated a transparent box 10 of conventional parallelepiped form. The box consists of an upper part 12 and a lower part 14. If desired, the lower part may be provided with a layer of foam plastic or the like to prevent jarring of the prosthesis or scratching of the protective cover due to abrasion. The parts of the box 10 may be hingeably connected or these parts may be removable from one another. They are preferably of a plastic of known type which is penetrable to X-ray radiation for purposes of sterilization as will be indicated hereinafter.

The heart valve itself is indicated generally at 16 as is also seen in FIGS. 2, 3, 4, 5 and 8. As perhaps is most clearly seen in FIG. 2, the valve 16 includes a ring-like structure 18 which is covered by a skirt 20. This skirt may be fabricated, for example, of Dacron and is intended to prevent, for example, thrombo embolisms as is, per se, well known.

Extending upwardly from the ring-like structure 18 is a cage 20, the purpose of which is to entrap a ball 22 which serves the function of opening and shutting the valve in well known manner.

The valve 16 is supported initially on a mandrel indicated generally at 30. The mandrel 30 constitutes a support which is known per se and which consists, for example, of a rod 32 extending axially through a hexagonal tube 34, the rod 32 being fabricated, for example, of a metal such as steel and the tube 34 being fabricated, for example, of Teflon.

The tube 34 is a one-piece tube including at its upper extremities a number of fingers 38 which are capable of being deflected radially outwards in order to bear outwardly against the ring-like structure 18 of valve 16 for purposes of engaging and supporting the same. For purposes of causing the fingers 36 to deflect radially outwards there is mounted on the end of the rod 32 a knob 38 which bears against the inner surfaces of the fingers 36 which are each provided with an inner cam surface (not shown) which cooperate with the knob 38 to cause the finger deflection referred to above.

Rod 32 threadably engages with the interior of the tube 34 so that rotation of rod 32 causes a longitudinal or axial progression of the rod 32 through the tube 34 thereby moving the knob 38 upwardly and effecting outward displacement of fingers 36.

As will be indicated hereinafter, reverse rotation of the rod 32 will retract the knob axially through the disposition of the fingers 36 allowing the fingers 36, which are resilient, to return to normal position whereat the fingers 36 will be disengaged from the ring-like structure 18 thereby freeing the valve 16 at a later state of the procedure.

The valve 16, mounted on the mandrel 30 as aforesaid, is encapsulated in the capsule 40. This capsule consists of at least two parts, one of which is indicated at 42 and the other of which is indicated at 44. The part 42 is provided with an opening and a collar 46, the collar 46 slipping over the tube 34 and having a press fit with the same as may be best seen, for example, in FIG. 6. The part 44 is mounted on the part 42 by a strip-removal device of known construction such as, for example, indicated at 48. This may be a pull-tab type device so that a simple manipulation can remove the strip 48 thereby permitting the part 44 to be removed from the part 42, thereby exposing the valve 16 for access. Strip 48 can also be an adhesive strip holding parts 42 and 44 together.

The capsule 40 is of a rigid material, preferably transparent and, for example, of a plastic such as polyethylene, polypropylene, polystyrene or the like. It is preferably sufficiently thick so as to be rigid and non-collapsible so that the capsule 40 is supported in entirety in a position spaced from and not touching the valve 16 at any part of the latter.

In the capsule 40 is provided an entry port 50 best seen, perhaps, in FIG. 7. This entry port is preferably intended to constitute a unilateral entrance path for a fluid such as, for example, a physiologic saline solution or a Ringers solution in which are, for example, contained an antibiotic such as penicillin and an anticlotting compound such as heparin. The use of these substances for the purposes intended are known per se but are not known for application in the manner indicated herein.

The port 50 may more particularly include a penetrable rubber stopper indicated at 52, and a thin plastic plate 54 which is perforated for purposes of permitting the flow of a fluid therethrough. For purposes of filtering, there may be provided a glass wool filter such as indicated at 56, which is held in position by a perforated disc 58 trapping the glass wool filter 56 against the perforated disc 40.

As illustrated in FIGS. 5 and 7 and as will be further alluded to hereinafter, a syringe 60 is employed for purposes of constituting a source of the aforenoted solution. The needle 62 of the syringe is inserted through the rubber disc 52 to discharge its fluid into the chamber 64 from whence under the effect of pressure generated by the plunger 66 of the syringe the fluid is urged through perforated disc 54, through filter 56 and into the interior chamber 66 of the capsule. It will, of course, be noted that the disc 58 is perforated in a manner similar to the disc 54 for purposes of permitting the entry of the fluid. At the same time, it will also be noted that withdrawal of the needle 62 from the rubber disc 52 will enable a resealing of the opening therein so that fluid will not be able to escape outwardly through the rubber stopper or disc 52.

The valve mounted on the mandrel and encapsulated within the capsule 40 is as a combination placed within a removable protective material such as indicated, for example, at 70 in FIGS. 1 and 3. The removable material 70 illustrated in FIGS. 1 and 3 is shown in the form of a collapsible plastic bag being preferably of polyethylene and being tied at the open end thereof such as indicated at 72. The purpose of this bag and its relationship with the capsule 40 will be explained in greater detail hereinafter. It should be noted, however, that the collapsible bag 70 is only one example of the protective device whch may be employed for this purpose. It is also possible to employ, for example, the rigid dumbbell-shaped protector indicated at 74 in FIG. 4, this being made of two reasonably rigid halves of transparent plastic such as polypropylene, polyethylene, polyvinyl or the like, the halves being snapped together.

The whole assembly is then placed for shipping in the box 10 mentioned hereinabove, which provides the physical protection for the part contained therein. It should be noted that the material from which the box 10, the protector 70 or 74, and the capsule 40 are made are penetrable to X-ray radiation for purposes of sterilization as will next be explained below.

The substantial beginning and end of the arrangement is illustrated in FIG. 8. FIG. 8 illustrates the general beginning of the arrangement and also illustrates the subsequent disposition of the arrangement prior to installation. More particularly, the valve 16 is mounted on the mandrel 30 and is then subjected to one of the cleaning operations described in my copending application Ser. No. 399,466 filed Sept. 21, 1973 and referred to hereinabove as including electrochemical cleaning, chemical cleaning, electropolishing and cathodic polishing. It will be noted that at this stage of the process, the part 42 of the capsule 40 is already installed on the tube 34 of the mandrel or support assembly. With the valve thusly cleaned and free from grease and other foreign substances, the mandrel is maintained in a dirt-free atmosphere and the part 44 of the capsule 40 is installed on the part 42 in hermetically sealed relationship thereto. Since the capsule does not touch the valve itself, and since the valve has been freed from all forms of "dirt," and is maintained free therefrom, the valve may be maintained in this condition until the surgical process for installation is ready to commence. To assist in maintaining the valve free from dirt, it should be noted that it is possible to insert an inert gas into the capsule.

At the same time, it is possible to have cleaned the rod 32 of the mandrel 30 as well as the outer part of the tube 34. The group of elements thusly processed up to this point may then be placed into a protective bag such as the bag 70 in FIG. 3 or in the protective casing 74 such as illustrated in FIG. 4. The thusly grouped components may then be further boxed in the box 10 as indicated hereinabove relative to FIG. 1.

At this point, the objects are ready for sterilization, and sterilization may be effected by subjecting the entirely packaged item to X-ray irradiation, for example, within a range of from about 3000 to 10,000 Rads. This irradiation will serve to sterilize not only the valve 16 but also the supporting mandrel. The cleaned and sterilized package is thus ready for shipment to a hospital for purposes of use and storage.

In the hospital, when the valve is subsequently required for a surgical procedure, the box is brought to a room adjacent the operating room whereat the box is opened and the packaged and mandrel-supported valve is offered, for example, to a scrub nurse. The scrub nurse takes the package and mandrel-supported valve from the box, brings it into an antiseptic environment, and then removes the package (e.g., the bag 70 or the case 74 in FIGS. 3 and 4 respectively). The nurse or some other surgical assistant now handles the mandrel 32 with a sterilized gloved hand. The nurse or some assistant may then use the syringe 60 as indicated in FIGS. 6 and 7 to inject into the interior of the capsule 40 a solution containing, as has been noted above by way of example, heparin and an antibiotic. The valve is permitted to bathe in this solution while initial surgical procedures are being effected.

When the surgical procedure has proceeded to the point where the valve is required for installation, the part 44 of the capsule is removed from the part 42 and the solution is thrown away or otherwise disposed of. The removal of the part 44 is preferably effected by the surgeon himself, thereby bringing the assembly to the condition illustrated in FIG. 8. In FIG. 8, the valve is illustrated as supported on the mandrel support 30. The valve is then sutured into position in a cardiac or vascular environment according to known techniques, whereupon the mandrel 30 can be removed and disposed of or utilized again in another packing procedure.

It will be noted that all components contained within the bag 70 or case 74 are in sterilized and in clean condition untouched by hands, whether gloved or otherwise, until the bag or casing is removed. Thereafter the valve itself remains both in sterile and untouched condition, and therefore free from foreign matter until the very last instant before installation at which time the valve is maneuvered to a site of installation by the use of the mandrel 32. The mandrel 32 is still in sterile condition. By this time, however, it has been touched by gloved hands and may or may not have foreign particles present thereon. These foreign particles, however, will not be installed into the patient, and therefore do not have any deleterious effect as regards the vascular or cardiac systems and cannot be instrumental in causing thrombosis or the like. As a result, the optimum treatment has been given to the valve to clean the same and maintain the same in perfectly cleaned condition in the principles of the invention.

The process for installing the valve itself is well known and is, for example, described in the article "Surgery of Multivalvular Cardiac Lesions" by Viking Olov Bjork, M.D. from the Thoracic Surgical Clinic, Karolinska Sjukhuset, Stockholm, Sweden. Reference can be made, for example, to FIG. 3 of the cited article demonstrating the Kay-Shiley disc valve prosthesis, and to FIGS. 5D and 5E illustrating the Bjork-Shiley aortic tilting disc valve.

From what has now been described hereinabove, it will now be appreciated that there is provided in accordance with the invention a method of packaging a prosthetic device for surgical use, said method comprising detachably coupling a support to a prosthetic device, cleaning substantially all foreign material from at least the device itself if not from the associated support, encapsulating the thusly cleaned device in an openable capsule with the support extending therethrough, and sterilizing the support with the thusly encapsulated and cleaned device thereon. Before sterilization, the support and cleaned device may be encased in a removable protective material. Furthermore, prior to sterilization, the thusly encased support and cleaned device may be placed in an openable box. The entire aggregation is sterilized by radiation techniques, such as, for example, by exposing the aggregation to X-ray radiation. The capsule may be filled with an inert gas. Provision is made for the unidirectional insertion of a solution containing an antibiotic and other necessary blood control drugs. The steps which are taken to package the device are all effected in a "clean" room. Shipment takes place in the triple container, and implantation can be effected without substantially any touching of the valve by even a sterilized gloved hand so that the benefits set forth in my copending application Ser. No. 399,466 are thoroughly experienced.

There will now be obvious to those skilled in the art many modifications and variations of the techniques and packaged arrangement set forth hereinabove. Such variations and modifications will not depart from the scope of the invention if lying within the scope of the following claims.

What is claimed is:

1. A method comprising mounting a prosthetic device on a support and removing at least substantially all foreign substance from the device and support, encapsulating the prosthetic device in a capsule, encasing said device and support in a removable shield, boxing the thusly encased device and support, irradiating the thusly boxed and encased device and support to sterilize the same, sequentially removing the box and shield, injecting a fluid into the capsule to treat the prosthetic device, opening the capsule to expose the device, and maneuvering the device by the use of the support to locate the device proximate a site of installation.

2. A method as claimed in claim 1 wherein said fluid is a liquid with an anti-biotic therein.

3. A method as claimed in claim 1 wherein the foreign substance is removed by electrochemical cleaning, chemical polishing, electropolishing or cathodic polishing.

4. A method as claimed in claim 1 wherein the shield is removed in a sterilized atmosphere.

5. A method as claimed in claim 1 wherein the prosthetic device is a heart valve including a ring, comprising suturing the ring in position in a cardiac system and detaching the support from the device.

* * * * *